(12) United States Patent
Pretre (10) Patent No.: US 10,101,186 B2
(45) Date of Patent: Oct. 16, 2018

(54) METHOD AND MEASURING APPARATUS FOR DETERMINING SPECIFIC QUANTITIES FOR GAS QUALITY

(71) Applicant: MEMS AG, Brugg (CH)

(72) Inventor: Philippe Pretre, Dattwil (CH)

(73) Assignee: MEMS AG, Brugg (CH)

( * ) Notice: Subject to any disclaimer, the term of this patent is extended or adjusted under 35 U.S.C. 154(b) by 313 days.

(21) Appl. No.: 14/939,756

(22) Filed: Nov. 12, 2015

(65) Prior Publication Data

US 2016/0138951 A1    May 19, 2016

(30) Foreign Application Priority Data

Nov. 14, 2014  (EP) .................................... 14003855

(51) Int. Cl.
| | |
|---|---|
| *G01F 1/66* | (2006.01) |
| *G01N 25/18* | (2006.01) |
| *G01N 29/024* | (2006.01) |
| *G01N 33/22* | (2006.01) |
| *G01N 7/00* | (2006.01) |
| *G01N 9/00* | (2006.01) |
| G01N 25/00 | (2006.01) |

(52) U.S. Cl.
CPC ................ *G01F 1/66* (2013.01); *G01N 7/00* (2013.01); *G01N 9/00* (2013.01); *G01N 25/18* (2013.01); *G01N 29/024* (2013.01); *G01N 33/225* (2013.01); *G01N 25/005* (2013.01); *G01N 2291/02836* (2013.01)

(58) Field of Classification Search
None
See application file for complete search history.

(56) References Cited

U.S. PATENT DOCUMENTS

| | | | | |
|---|---|---|---|---|
| 2,591,759 A | * | 4/1952 | Zaikowsky | .......... G01N 27/185 422/98 |
| 6,786,633 B2 | * | 9/2004 | Wallen | ................... G01K 11/24 374/117 |
| 2002/0105999 A1 | * | 8/2002 | Wallen | ................... G01K 11/24 374/117 |

FOREIGN PATENT DOCUMENTS

| | | |
|---|---|---|
| EP | 0 715 169 | 6/1996 |
| EP | 2 015 056 | 1/2009 |
| EP | 2574918 | 4/2013 |
| EP | 2 806 271 A1 | 11/2014 |
| EP | 2806271 | 11/2014 |
| WO | 02/40992 | 5/2002 |

(Continued)

OTHER PUBLICATIONS

European Search Report cited in EP 15 00 3229, dated Mar. 4, 2016, two pages.

(Continued)

*Primary Examiner* — Paul D Lee
(74) *Attorney, Agent, or Firm* — Nixon & Vanderhye P.C.

(57) ABSTRACT

A method and a measuring apparatus for determining specific quantities for the gas quality in which the gas or gas mixture flows through an ultrasonic flow sensor as well as through a microthermal sensor, and the former is used for determining the sound and flow velocity and the latter for determining the thermal conductivity and the thermal capacity of the gas or gas mixture. The sound velocity, the thermal conductivity and the thermal capacity are subsequently used for the correlation of the specific quantities for the gas quality.

17 Claims, 10 Drawing Sheets

(56) References Cited

FOREIGN PATENT DOCUMENTS

WO     2004/008136     1/2004

OTHER PUBLICATIONS

European Search Report cited in EP 14003855.5, dated Jan. 1, 2015, six pages.
Matter, Daniel et al., Microelectronic Domestic Gas Meter with New Technology, Technisches Messen 71, pp. 137-147 2004.
Huang, K., Statistical Mechanics, Mass. Inst. of Tech., John Wiley & Sons, pp. 112-113, (1987).
Lynnworth, L.C. et al., Ultrasonic flowmeters: Half-century Progress Report, 1955-2005, ScienceDirect, Ultrasonics 44, pp. e1371-e1378 (2006).

\* cited by examiner

METHOD AND MEASURING APPARATUS FOR DETERMINING SPECIFIC QUANTITIES FOR GAS QUALITY

RELATED APPLICATION

This application claims priority to European Patent Application No. 14003855.5 filed Nov. 14, 2014, the entirety of which is incorporated by reference.

BACKGROUND OF THE INVENTION

The invention relates to a method and a measuring apparatus for determining specific quantities for the gas quality or energy consumption in domestic and industrial areas.

The (natural) gas composition and thus the gas quality will fluctuate more frequently and strongly in future due to new sources of origin (biogas, liquefied gas from all regions of the world, hydrogen from the exploitation of excess current from the generation of alternative energy) and will thus have different effects on gas application processes, which may also include such that are negative. The processes could be adjusted to the fluctuating gas quality by direct measurement of specific quantities for the on-site gas quality in order to ensure optimal and secure operation. The specific quantities for gas quality include e.g. the Wobbe index for burner control units, the air-to-fuel ratio in power generation systems (industrial furnaces, fuel cells etc.), the methane number for gas motors, or the calorific value for billing the purchased energy quantity. The latter requires however that the purchased gas quantity is measured, which currently occurs, apart from a few exceptions, by means of volumetric flow measurements with diaphragm gas meters (domestic) or, in the case of purchasers of large gas volumes (industry), by means of rotary displacement meters, turbine wheel meters, or ultrasonic flow meters. All these measuring means are only suitable for determining the operating volume. In order to draw conclusions from these data on the purchased, billable energy, it is necessary to provide a conversion to standard volume and also to have information on the calorific value of the respectively supplied gas. Both occur only imprecisely: the standard volume is usually calculated with a mean temperature and a mean pressure, and the calorific value is also a value averaged over the billing period.

A method is known from the patent application EP 14001767 in which a flow is generated by a critical nozzle in order to determine specific quantities for the gas quality by means of a downstream microthermal sensor. Said method requires that critical pressure conditions prevail at all times via the nozzle, either by supplying the nozzle with an upstream pressure or by generating a vacuum behind the nozzle. The method is therefore not directly suitable for determining specific quantities for the gas quality at the end customer, because the supply networks at this point rarely have the required upstream pressure and the installation of a vacuum pump behind the nozzle is out of question.

A method is known from EP 2 574 918 A1, in which a microthermal sensor is used to upgrade a volumetric flow measuring device in the respect that the thermal diffusivity can be determined, which in the case of known thermal conductivity allows a classification of the gases into L(ow calorific) or H(igh calorific) gases. It is, however, not possible to draw conclusions with sufficient precision on the calorific value and the energy flow from the volumetric flow, thermal diffusivity and thermal conductivity.

SUMMARY OF THE INVENTION

A method and measuring apparatus have been invented with which specific quantities for the gas quality or the power consumption can be determined in real time.

The method and measuring apparatus may be used to remedy the disadvantages of the aforementioned methods and to provide a method and a measuring apparatus which are suitable for low-pressure gas networks and by means of which it is also possible to determine the calorific value and energy consumption, in addition to the classification of the gases into L or H gases.

The method and measuring apparatus may include an ultrasonic flow sensor with a microthermal sensor for determining specific quantities for the gas quality or energy consumption as follows.

Measurement of sound velocity and volumetric flow may be made using the ultrasonic flow sensor: For determining the volumetric flow, an ultrasonic signal is typically injected into the flow medium at an angle transversely to the direction of flow and the runtime difference of the ultrasonic signal is measured both in the direction of flow and against said direction of flow (FIG. 1b). The runtime difference of the two ultrasonic signals is then a measure for the average flow velocity, from which the volumetric flow can be calculated with the known line cross-section:

$$v_x = \frac{L}{2 \cdot \cos\alpha \cdot t_{12} \cdot t_{21}} (t_{21} - t_{12}); \quad (1)$$

$$c_s = \frac{L}{2 \cdot t_{12} \cdot t_{21}} (t_{21} + t_{12}).$$

wherein
$v_x$—is mean flow velocity,
$c_s$—is sound velocity,
L—is a length of the measuring distance,
$t_{12}$—is runtime in the direction of flow, and
$t_{21}$—is runtime against the direction of flow.

The sum total of the runtimes contains information on the sound velocity $c_s$ of the medium, which in ultrasonic flow meters is mostly not used any further.

In combination with a microthermal sensor as described in the patent application EP 14001767, it is possible to omit the critical nozzle due to the information on the sound velocity, because the latter also supplies the sound velocity in first order, with the advantage that no critical pressure conditions are necessary, i.e. it is possible to measure at given pressure. Consequently, neither compressors nor vacuum pumps are required in low-pressure gas networks.

Determining the Mass Flow:

The density can be determined from the sound velocity by correlation, which density correlates well with the sound velocity for most gases. In order to further improve correlation of the density, thermal conductivity can additionally be measured at one or several temperatures and can be included in the correlation.

The mass flow is proportional to the product $\rho \cdot v_x$ from density $\rho$ and the flow velocity $v_x$:

$$\dot{m} = \rho \cdot v_x \cdot A, \quad (2)$$

wherein A means the cross-section of the flow channel.

Measurement of thermal conductivity by means of the microthermal sensor:

Integrated CMOS hot-wire anemometers allow both microthermal thermal conductivity measurement and also mass flow measurement. Reference in connection with this technology is made to D. Matter, B. Kramer, T. Kleiner, B. Sabbattini, T. Suter, "Mikroelektronischer Haushaltsgaszahler mit neuer Technologie" [Microelectronic domestic gas meter with new technology], Technisches Messen 71, 3 (2004), p. 137-146.

For the purpose of describing microthermal measurements, the one-dimensional thermal conduction equation is used which describes the microthermal system (Kerson Huang: Statistical Mechanics, 2nd Edition, John Wiley & Sons, New York 1987, ISBN 0-471-85913-3):

$$\frac{c_p}{\lambda} \cdot \rho v_x \cdot \frac{d}{dx} T = \nabla^2 T + \frac{1}{\lambda} \Theta, \quad (3)$$

wherein
$v_x$—is a component of the mean flow velocity (velocity vector) in the X direction, i.e. along the gas flow,
T—is temperature, $$\frac{d}{dx} T$$

—is a temperature gradient,
$c_p$—is a thermal capacity of the gas at constant pressure,
$\rho$—is density,
$\lambda$—is a thermal conductivity of the gas, and
$\nabla^2 T$—is a Laplace operator, applied to the temperature T, wherein $$\nabla^2 = \left(\frac{d}{d_x}\right)^2 + \left(\frac{d}{dy}\right)^2 + \left(\frac{d}{dz}\right)^2.$$

Since the gas (gas flow) only flows in the X direction, the components $v_y$ and $v_z$ in the Y direction and in the Z direction of the mean flow velocity $\vec{v}$ are assumed to be zero (0). $\Theta$ with the unit Watt/m³ describes the source term of the heating element. The source term originates in the microthermal method from the heating wire of a miniaturised, integrated heat-wire anemometer, which supplies thermal energy into the system.

Notice must be taken that the thermal conductivity $\lambda$ acts separately on the solution of the equation (3) due to the source term $\Theta$. Conversely, the thermal conductivity can be determined when the microthermal sensor is used without mass flow applied ($v_x=0$ and $\dot{m}=0$). The relevant differential equation for the temperature distribution is then simply $$\nabla^2 T = -\frac{1}{\lambda} \Theta. \quad (4)$$

Furthermore, the temperature distribution can be changed by varying the source term, which allows the determination of the thermal conductivity at different temperatures.

Determination of thermal capacity by means of a microthermal sensor:

The solution of the equation (3), which describes the temperature distribution in the microthermal system, allows determining the flow factor $\varphi$ by measuring said temperature distribution, $$\varphi := \frac{c_p}{\lambda} \cdot \rho \cdot v_x = \frac{c_p}{\lambda} \cdot \frac{\dot{m}}{A}, \quad (5)$$

wherein A designates the cross-section of the flow channel over the microthermal sensor and $\dot{m}$ the mass flow. The thermal capacity can finally be determined with the known mass flow and the known thermal conductivity.

Correlation of the specific quantities for the gas quality:

Three independent measured quantities are available with the sound velocity $c_s$, the thermal conductivity $\lambda$ and the thermal capacity $c_p$, with which specific quantities Q for the gas quality such as the calorific value can now be correlated by means of a correlation function $f_{corr}$:

$$Q = f_{corr}(\text{sensor output}) := f_{corr}(S_{out}). \quad (6)$$

The "sensor output" $S_{out}$ is a function of the output quantities $c_s$, $\lambda$ and $c_p$:

$$S_{out} = f(c_s, \lambda, c_p) \quad (7)$$

Figure 2A:
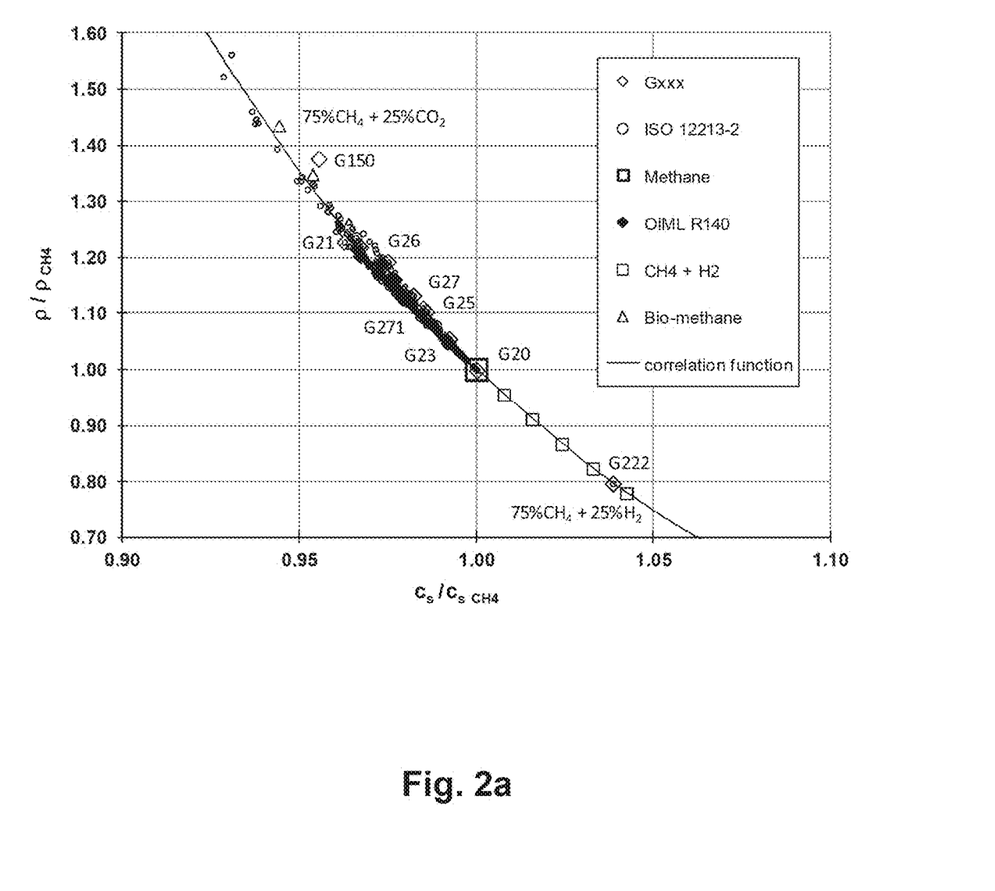
FIG. 2a shows an example of density determination (correlation) on the basis of sound velocity.

The following correlation function is obtained for example for the correlation of the density ratio $Q = \rho/\rho_{ref}$ at 0° C. and 1013.25 mbar shown in FIG. 2a:

$$\rho_{corr}/\rho_{ref} = f_{corr}(S_{out}) = a_0 + a_1 \cdot S_{out} + a_2 \cdot S_{out}^2 \quad (8a)$$

with coefficients $a_0=36$, $a_1=-65$ and $a_2=30$ and methane (G20) as reference. $S_{out}$ is simply the sound velocity $c_s$:

$$S_{out} = f(c_s, \lambda, c_p) c_s. \quad (9a)$$

Figure 2B:
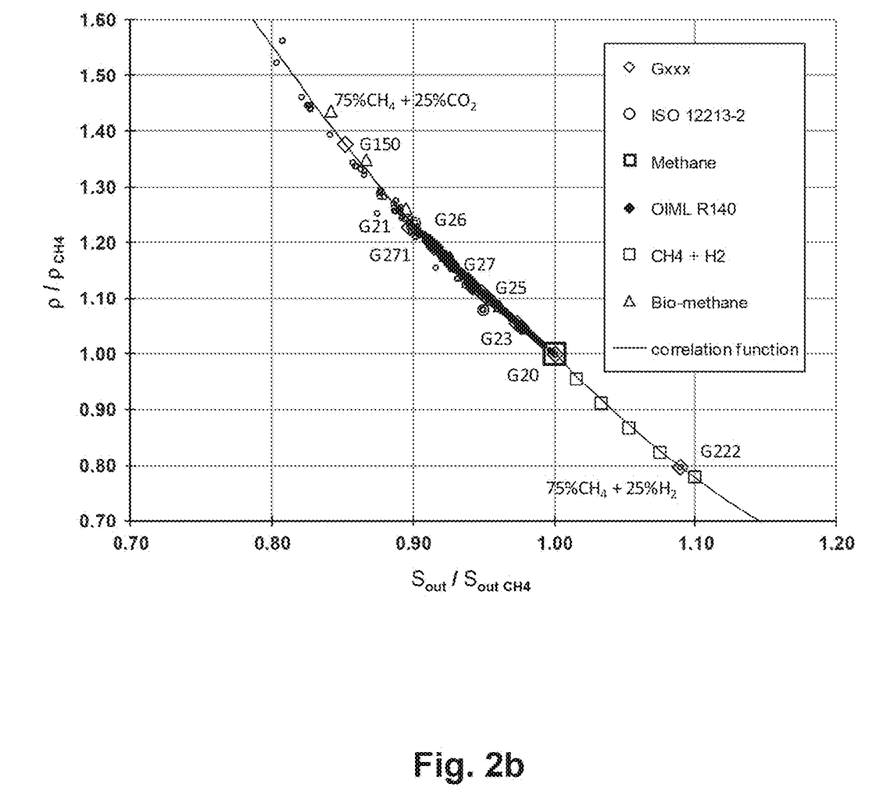
FIG. 2b shows an example of improved density determination (correlation) on the basis of the sound velocity and the thermal conductivity.

FIG. 2b shows an improved correlation of the density ratio $Q = \rho/\rho_{ref}$ at 0° C. and 1013.25 mbar on the basis of the sound velocity and the thermal conductivity, measured at two different temperatures.

In the event of the correlation of specific quantities for the gas quality in FIG. 3a, the equation (8a) for the example of calorific value is read as follows:

$$CV/CV_{ref} = f_{corr}(S_{out}) = a_0 + a_1 \cdot S_{out} + a_2 \cdot S_{out}^2 \quad (8b)$$

with coefficients $a_0=8.1$, $a_1=-11$ and $a_2=4.7$ and methane (G20) as reference again. $S_{out}$ is now a function of all three output quantities:

$$S_{out} = f(c_s, \lambda, c_p) = \left(\frac{c_p}{c_{p,ref}}\right)^{-0.86} \cdot \left(\frac{\lambda}{\lambda_{ref}}\right)^{0.22} \cdot \frac{c_s}{c_{s,ref}}. \quad (9b)$$

Figure 3A:
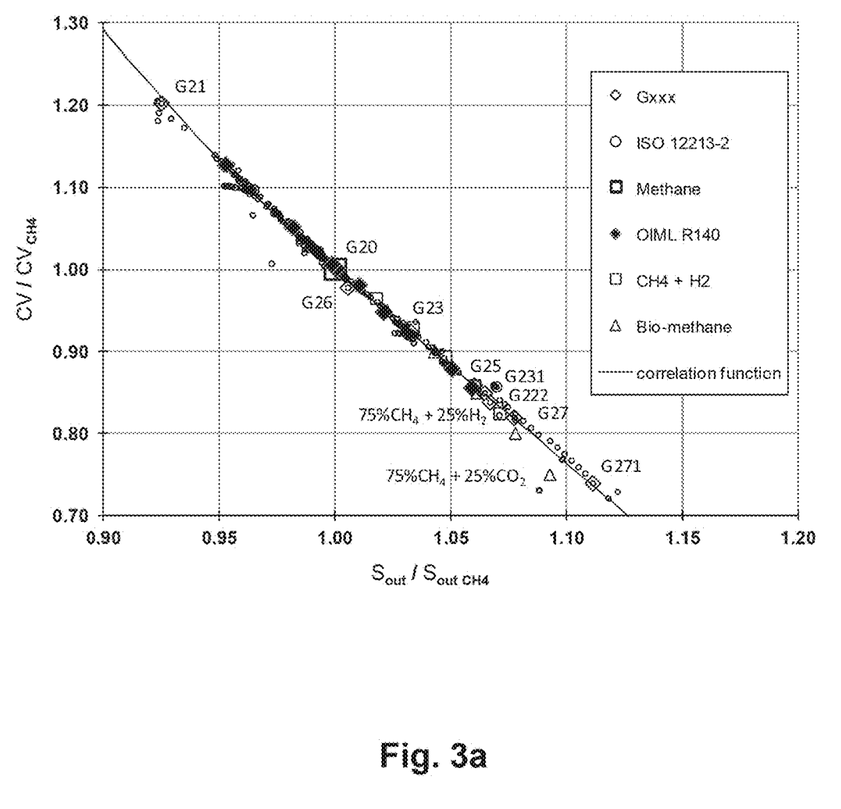
FIG. 3a shows an example of calorific value determination (correlation) on the basis of the thermal capacity, the thermal conductivity and the sound velocity.

It is easily comprehensible from the results in FIG. 2a and FIG. 3a that the Wobbe index W as a measure for the power of a burner, defined as $$W := \frac{CV}{\sqrt{\rho_{gas}/\rho_{air}}}, \quad (10)$$

can be correlated by means of $c_s$, $c_p$ and $\lambda$ as further gas quality in that the equations (8a) for the density and (9b) for the calorific value are combined with each other.

As a further example, the Z or real gas factor as a gas quality can be correlated from the three independent quantities of sound velocity $c_s$, thermal conductivity $\lambda$ and thermal capacity $c_p$, which factor describes the deviation of the behaviour of a real gas from the ideal gas law, $$p \cdot V = Z \cdot R_m \cdot T. \tag{11}$$

Figure 3B:
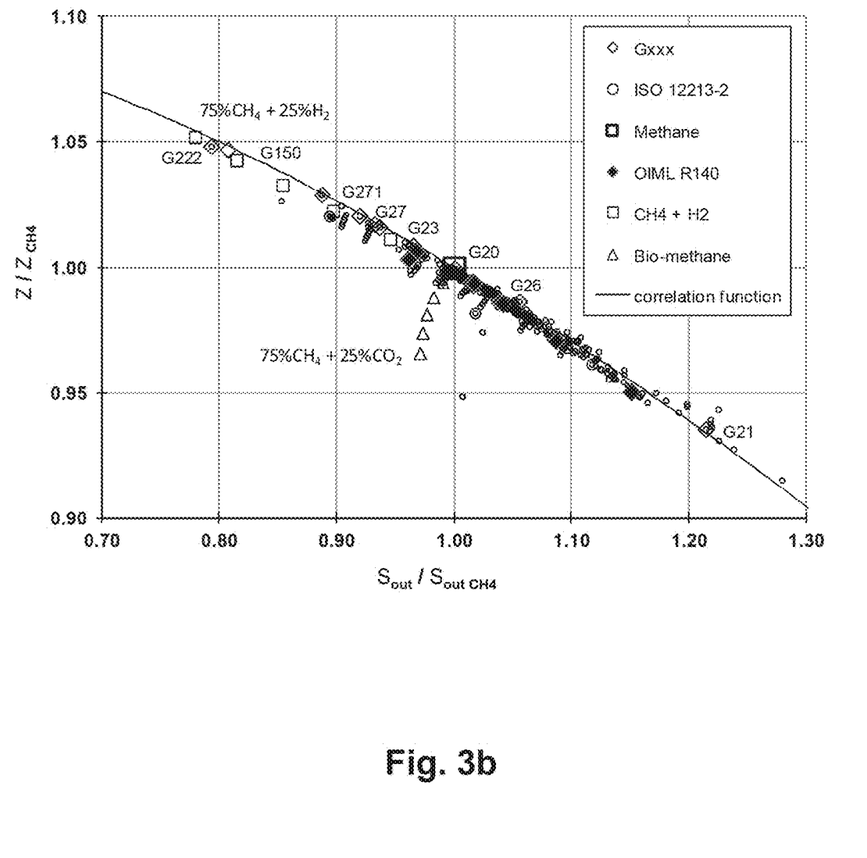
FIG. 3b shows an example for the determination of the Z factor (correlation) on the basis of the thermal capacity, the thermal conductivity and the sound velocity.

The real gas behaviour strongly deviates from the ideal gas behaviour especially at higher pressures, i.e. precisely at pressures as they occur in large gas transport lines (and therefore need to be taken into account in particular). Of interest in this application is the fact that the determination of the independent quantities need not occur at the same high pressure, but can also occur for example at ambient pressure, where the setup of a respective measuring apparatus can be implemented in a much easier way. FIG. 3b shows a possible correlation of the Z factor for 50 bars with the following basic parameters:

$$Z/Z_{ref} = f_{corr}(S_{out}) = a_0 + a_1 \cdot S_{out} + a_2 \cdot S_{out}^2 + a_3 \cdot S_{out}^3 \tag{8c}$$

with coefficients $a_0=1.1$, $a_1=0.15$, $a_2=-0.29$ and $a_3=0.05$ and methane (G20) as reference. $S_{out}$ is again a function of all three output quantities (at ambient pressure):

$$S_{out} = f(c_s, \lambda, c_p) = \left(\frac{c_p}{c_{p,ref}}\right)^{1.35} \cdot \left(\frac{\lambda}{\lambda_{ref}}\right)^{-0.25} \cdot \left(\frac{c_s}{c_{s,ref}}\right)^{-2}. \tag{9c}$$

Figure 3C:
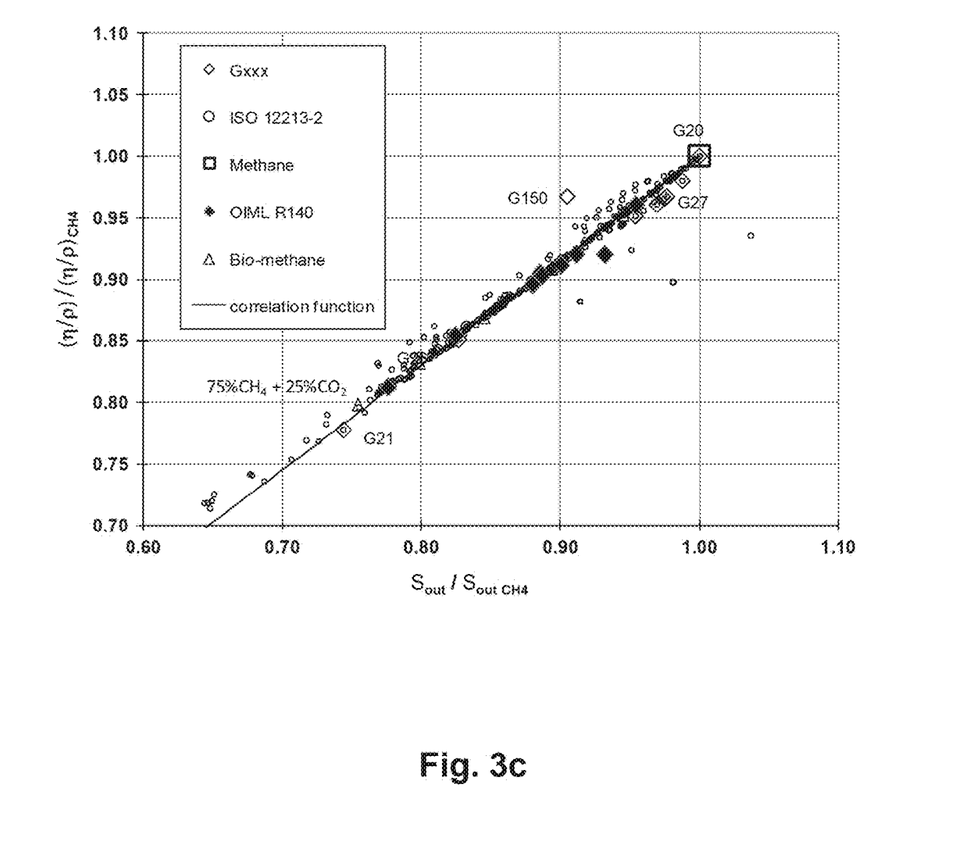
FIG. 3c shows an example for the determination of the kinematic viscosity (correlation) on the basis of the thermal capacity, the thermal conductivity and the sound velocity.

A further example to be mentioned is the correlation of the kinematic viscosity, $\eta/\rho$ (viscosity/density). This quantity is found again in the Reynolds number, Re, which is used in fluid mechanics and can be understood as the ratio of inertia forces to viscous forces:

$$Re = \frac{\rho \cdot v \cdot d}{\eta} \tag{12}$$

wherein $\rho$ means the density, $v$ the flow velocity of the gas in relation to the body in the flow, and $d$ the characteristic length of the body. It therefore follows that the turbulence behaviour of similar bodies is identical with the same Reynolds number. With known kinematic viscosity it can thus be estimated for example when turbulence occurs in a gas in a piping system, which in the case of gas distribution networks is an important input for the configuration of such networks. FIG. 3c shows the correlation between the kinematic viscosity $\eta/\rho$ and the sensor output $S_{out}$:

$$(\eta/\rho)/(\eta/\rho)_{ref} = f_{corr}(S_{out}) = a_0 + a_1 \cdot S_{out} \tag{8d}$$

with coefficients $a_0=0.15$ and $a_1=0.85$ and methane (G20) as the reference. $S_{out}$ is again a function of all three output quantities:

$$S_{out} = f(c_s, \lambda, c_p) = \left(\frac{c_p}{c_{p,ref}}\right)^{-0.65} \cdot \left(\frac{\lambda}{\lambda_{ref}}\right)^{1.5} \cdot \left(\frac{c_s}{c_{s,ref}}\right)^{1.5}. \tag{9d}$$

Notice must be taken that the selection of $S_{out}$ on the one hand and also of $f_{corr}$ on the other hand are by no means predetermined, but are freely selected in such a way that the resulting correlation error becomes as small as possible. The polynomial function mentioned in the equations (8a) to (8d) is a typical selection which usually is successful, whereas the equations (9a) to (9d) rather attempt to describe the physical interrelationship.

In order to demonstrate that the method according to the present invention is not limited to the aforementioned examples, further examples of specific quantities for the gas quality are mentioned below which can be determined by the method:

The methane number, which is an important indicator in gas motor drives for the knocking tendency of a gaseous fuel, which gas motor drives can be used either in a stationary manner (e.g. in heat-power cogeneration plants) or in the motive field (e.g. in gas vehicles, ships etc).

The "air-to-fuel ratio" and thus the quantity of air to be supplied to the process. The knowledge of the "air-to-fuel ratio" is relevant for example in combustion processes, either stoichiometric (e.g. in combustion plants) or with excess air (e.g. in lean-burn engines), with open flame or of catalytic type (e.g. in reformation processes in high-temperature fuel cells) in order to optimise both the efficiency of the combustion process and also the exhaust behaviour.

The methane content, the monitoring of which is important in the process industry for example. In biogas plants, the methane content is typically monitored in the raw biogas (e.g. as a measure for the fermenter efficiency) and/or in the gas which is to be supplied to the natural gas network (e.g. for quality control) or in the residual gas discharged to the air (mainly carbon dioxide with as little methane as possible, since the latter has a high greenhouse effect).

Method Steps in a Typical Embodiment:

Measurement of pressure p and temperature T of the gas.

Ultrasonic determination of the volumetric flow proportional to the flow velocity $v_x$ and of the sound velocity $c_s$, which for most gases correlates well with the standard density $\rho_{norm}$.

Inclusion of the thermal conductivity $\lambda_{Ti}$ measured with the microthermal sensor (at one or several temperatures $T_i$) to further improve the correlation of the standard density $\rho_{norm}$.

Calculation of the density under operating conditions according to $$\rho = \rho_{norm} \cdot \frac{T_{norm} \cdot p}{p_{norm} \cdot T}. \tag{13}$$

Use of this information ($v_x$, $\varphi$ for determining the mass flow $\dot{m}$ proportional to $\rho \cdot v_x$ and, together with the thermal conductivity $\lambda$ and the flow factor $\varphi$ measured with the microthermal sensor, the thermal capacity $c_p$.

Correlation of the desired specific quantity for the gas quality, in particular of the calorific value CV, from the sound velocity $c_s$, thermal conductivity $\lambda$ and thermal capacity $c_p$.

The energy consumption $\Phi_{En}$ can be determined if necessary from the multiplication of mass or volumetric flow respectively with the calorific value CV (in J/kg or J/m$^3$).

The aforementioned standard density $\rho_{norm}$ shall be understood in this description as the density at a designated temperature $T_{norm}$ and a designated pressure $p_{norm}$. The standard density is usually stated at 0° C. and 1013.25 mbar. It is also possible to determine other values for the temperature $T_{norm}$ and the pressure $p_{norm}$ for which the correlation between density and sound velocity is known.

In the method for determining specific quantities for the gas quality according to an embodiment of the present invention:

a gas or gas mixture flows through an ultrasonic flow sensor and over a microthermal sensor, wherein the temperature and pressure of the gas or gas mixture are detected;

the flow velocity or volumetric flow as well as the sound velocity of the gas or gas mixture are determined by the ultrasonic flow sensor;

the density of the gas or gas mixture is correlated from the sound velocity;

the density information, together with the flow velocity, are used for calculating the mass flow;

the thermal conductivity of the gas or gas mixture at one or several temperatures is determined by means of the microthermal sensor;

the flow factor is calculated from the flow signal of the microthermal sensor in order to determine therefrom, together with the information of the mass flow and thermal conductivity, the thermal capacity or a quantity of the gas or gas mixture dependent on the thermal capacity; and the sound velocity, the thermal capacity at one or several temperatures, and either the thermal capacity or the quantity depending on the thermal capacity are used for the correlation of specific quantities for the gas quality, in particular of the calorific value.

The sound velocity determined with the ultrasonic flow sensor can be converted if necessary to the sound velocity at standard temperature.

In an advantageous embodiment, the thermal conductivity determined by means of the microthermal sensor at one or several temperatures is used together with the sound velocity for the preciser correlation of the density.

The density correlated from the sound velocity or from the sound velocity and thermal conductivity can be the standard density for example. The density or standard density correlated from the sound velocity or from the sound velocity and thermal conductivity is advantageously converted with the temperature and the pressure of the gas or gas mixture to the density under operating conditions.

In an advantageous embodiment of the method, the sound velocity, thermal conductivity at one or several temperatures and either the thermal capacity or the quantity dependent on the thermal capacity are used for correlation of the calorific value or Wobbe index (W) or Z factor or the kinematic viscosity.

In a further advantageous embodiment of the method, the energy consumption is calculated from the calorific value, together with the volume or mass flow, e.g. in that the product from volumetric or mass flow and calorific value is integrated up over time.

The aforementioned method and the aforementioned embodiments and variants are suitable both for continuous and also intermittent determination of specific quantities for the gas quality or of energy consumption.

The measuring apparatus for determining specific quantities for the gas quality or energy consumption according to the present invention comprises an evaluation unit which is set up for carrying out a method according to one of the aforementioned embodiments and variants, and an ultrasonic flow sensor for measuring sound and flow velocity, a pressure sensor for measuring the pressure, a temperature sensor for measuring the temperature, and a microthermal sensor for measuring the thermal conductivity and either the thermal capacity or a quantity of the gas or gas mixture dependent on the thermal capacity.

In a first embodiment of the measuring apparatus, the ultrasonic flow sensor and the microthermal sensor are arranged in a gas line and can be supplied with the same mass flow.

In a second embodiment of the measuring apparatus, the ultrasonic flow sensor is arranged in a main gas line and the microthermal sensor in a bypass gas line to the main gas line, wherein an element is provided in the main gas line which produces a pressure drop in order to generate a mass flow in the bypass gas line.

The ultrasonic flow sensor is advantageously placed not invasively on the gas line or main gas line in the first and second embodiment.

In a third embodiment of the measuring apparatus, the ultrasonic flow sensor and the microthermal sensor are arranged in a bypass gas line to a main gas line, wherein an element is provided in the main gas line which produces a pressure drop in order to generate a mass flow in the bypass gas line.

The splitting ratio between mass flow in the bypass gas line and the main gas line is advantageously known in the second and third embodiment, e.g. by calibrating with a known gas.

Irrespective of the embodiment and the variant, the measuring apparatus can additionally comprise a section of the gas line or main gas line or a bypass gas line in which at least one of the sensors of the measuring apparatus is arranged, or an element producing a pressure drop in the main gas line.

The evaluation unit advantageously forms a modular unit together with the remaining measuring apparatus. Depending on the application, the measuring apparatus can form a modular unit even without the evaluation unit, wherein the evaluation unit can be formed in a separate or higher-level computing unit.

The method and the measuring apparatus according to the present invention for determining specific quantities for the gas quality or the energy consumption offer the advantage that they can also be used in low-pressure gas networks without requiring an additional compressor or an additional vacuum pump, as provided for in the measuring apparatus described in the patent application EP 14001767.

It is further advantageous that the thermal conductivity of the gas or gas mixture at one or several temperatures determined by means of the microthermal sensor can be used, together with the sound velocity, for the preciser correlation of the density, which leads to preciser values for the mass flow.

The correlation of specific quantities for the gas quality from the three independent variables of sound velocity, thermal conductivity and thermal capacity further allows a higher precision in the determination of the calorific value and the energy consumption than is possible with the initially described method according to EP 2 574 918 A1.

SUMMARY OF THE DRAWINGS

The invention is explained below in closer detail by reference to the drawings, wherein.

DETAILED DESCRIPTION OF THE INVENTION

Figure 1A:
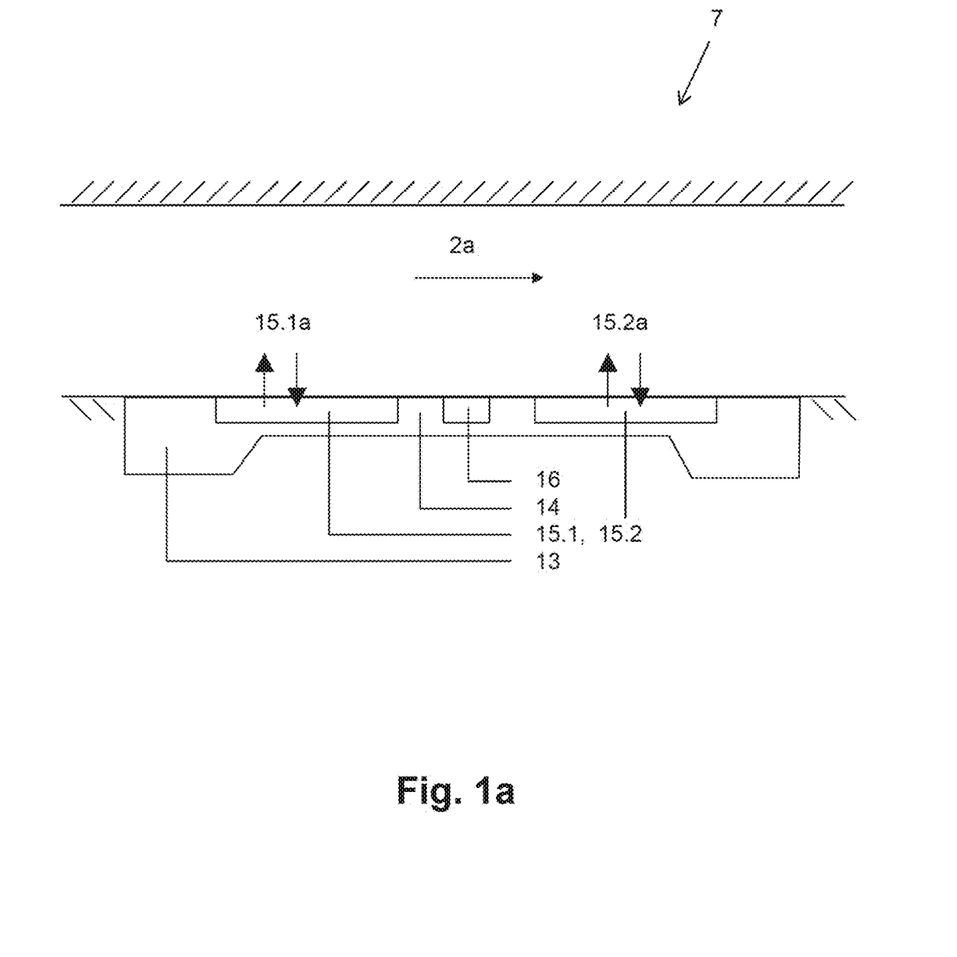
FIG. 1a shows the schematic configuration of an embodiment of a microthermal anemometer.
Figure 1B:
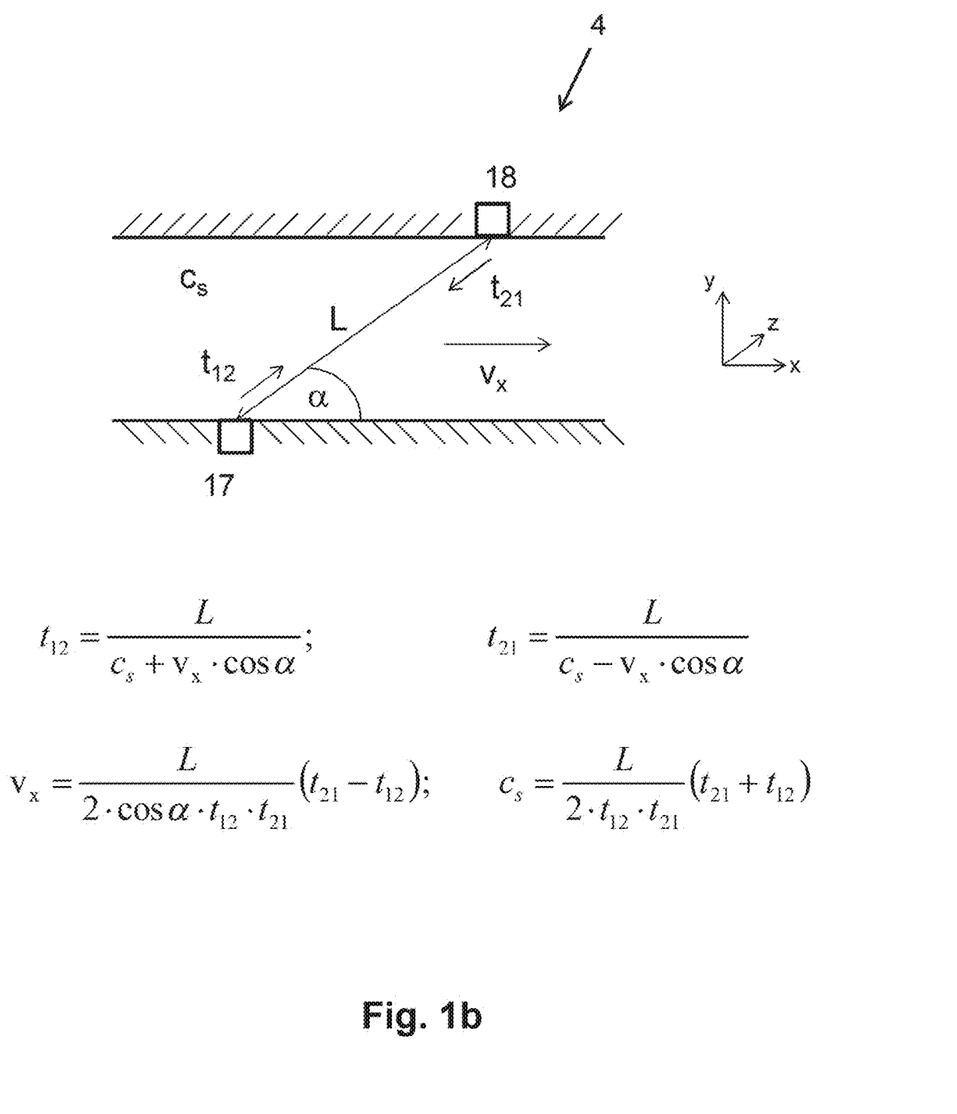
FIG. 1b shows a schematic illustration of an ultrasonic flow sensor.

FIG. 1a shows an embodiment of a microthermal sensor 7 for use in a measuring apparatus according to the present invention. As shown in FIG. 1a, the microthermal sensor can be an integrated, microthermal CMOS heat-wire anemometer, which in operation is arranged in a section of a bypass gas line and can be supplied with a gas or gas-mixture flow 2a. The microthermal CMOS heat-wire anemometer comprises a substrate 13, which typically contains a membrane 14 with a thickness of a few micrometers. The CMOS heat-wire anemometer further comprises two thermocouples 15.1, 15.2 and a heating element 16 which can be arranged in the direction of flow between the two thermocouples. The temperature can be detected by means of the thermocouples 15.1, 15.2, which temperature is obtained as a result of the heat exchange 15.1a, 15.2a with the gas or gas mixture flow 2a.

For further details concerning the functionality of the integrated microthermal CMOS heat-wire anemometer, reference is made to D. Matter, B. Kramer, T. Kleiner, B. Sabbattini, T. Suter, "Mikroelektronischer Haushaltsgaszahler mit neuer Technologie" [Microelectronic domestic gas meter with new technology], Technisches Messen 71, 3 (2004), p. 137-146.

FIG. 1b shows an embodiment of an ultrasonic flow sensor 4 for use in a measuring apparatus according to the present invention. For example, two units 17 and 18 which both generate and receive sound (e.g., piezo actuators or receptors) are arranged on obliquely opposite positions on the measuring line. A sound pulse emitted by the actuator 17 reaches the receptor 18 more rapidly than a sound impulse emitted simultaneously by the actuator 18 reaches the receptor 17. Both the sound velocity $c_s$ and also the flow velocity $v_x$ can be calculated from the runtimes $t_{12}$ and $t_{21}$, together with geometry factors of the arrangement.

For further details concerning the functionality of the ultrasonic sensor, reference is hereby made to L. C. Lynnwortha, Yi Liub, "Ultrasonic flowmeters: Half-century progress report, 1955-2005" in Ultrasonics, 44, Supplement (2006), p. e1371-e1378.

Figure 4:
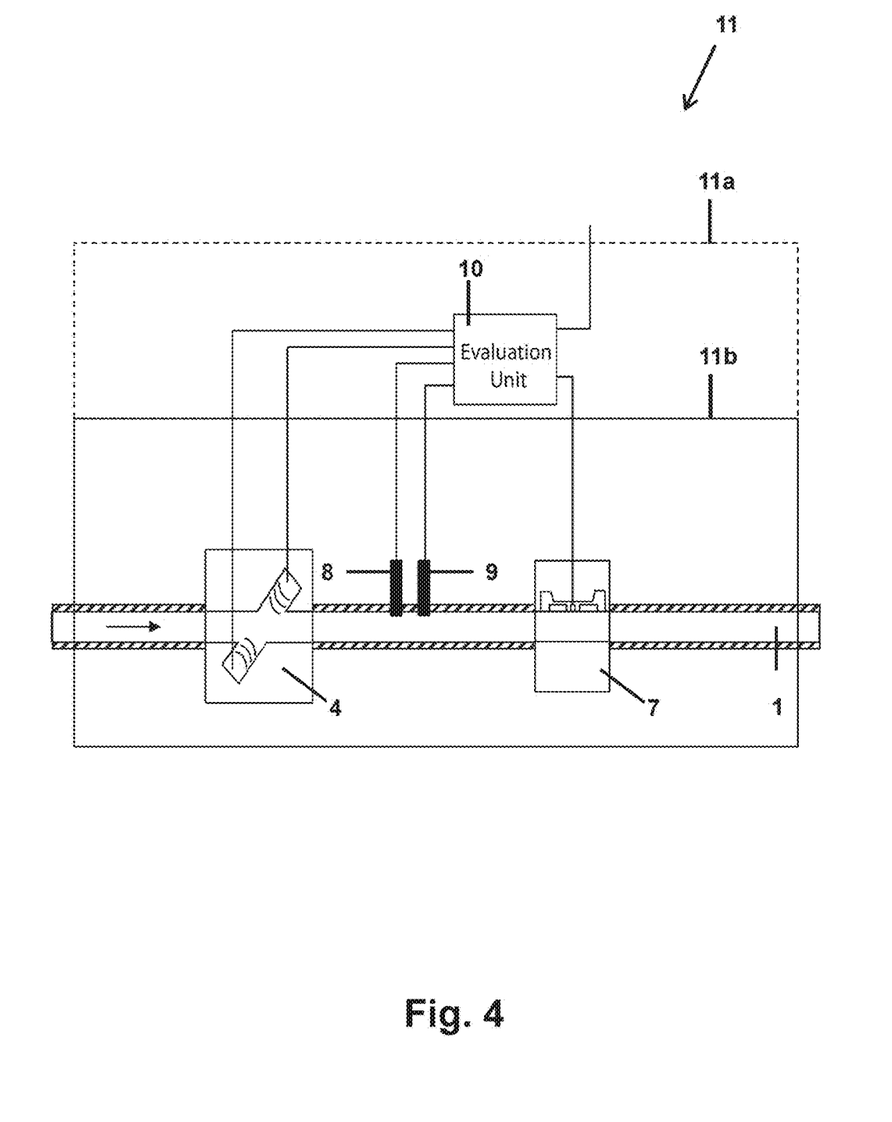
FIG. 4 shows an embodiment of the schematic configuration of a measuring apparatus according to the present invention in the main gas line.

FIG. 4 shows an embodiment of the schematic configuration of a measuring apparatus according to the present invention. In the embodiment, the measuring apparatus 11 comprises an evaluation unit 10 which is set up for carrying out a method according to the present invention, an ultrasonic flow sensor 4, a microthermal sensor 7, as well as a pressure sensor 8 and a temperature sensor 9, wherein the sensors can be arranged in a gas line 1. Some of these components or all of these components can be combined into a modular unit, wherein the evaluation unit 10 can be a component of the said modular unit (variant 11a), or the evaluation unit can be attached separately (variant 11b), e.g. in a higher-level computing unit.

The configuration of the embodiment shown in FIG. 4 is especially suitable for the determination of specific quantities for the gas quality in small and minute gas flows, as occur in the field of gas analyses for example, and where primarily the information concerning the gas quality is relevant.

The measuring apparatus in the embodiment shown in FIG. 4 can be used for example as an analytical unit or as a separate analytical device, wherein the analytical unit or the analytical device advantageously contains a gas line 1 in which the sensors 4, 7, 8, 9 of the measuring apparatus are arranged. Gas samples can be taken and analysed with the analytic unit or the analytic device. The connections and valves necessary for this purpose are not shown in FIG. 4.

An embodiment of the method for determining specific quantities for the gas quality of a gas and gas mixture according to the present invention will be described below with reference to FIG. 4. In this method, the gas or gas mixture flows in the gas line 1 through an ultrasonic flow sensor 4 and over a microthermal sensor 7. Pressure and temperature of the gas or gas mixture, i.e. the operating conditions, are determined with a pressure sensor 8 and a temperature sensor 9 additionally arranged in the gas line. The ultrasonic sensor further measures the sound velocity and the flow velocity or volumetric flow. Correlation of the density occurs subsequently on the basis of the sound velocity, wherein the density determined by means of correlation is appropriately converted to the density at the given temperature and the given pressure (operating conditions).

Furthermore, the thermal conductivity of the gas at one or several temperatures is measured with the microthermal sensor 7, in that the heating power of the heating wire is varied. If necessary, the result of this measurement can also be included in the correlation of the density. The mass flow is subsequently calculated from the value of the density and the volumetric flow. The ratio between thermal capacity and thermal conductivity of the gas is calculated from the flow factor, which is also measured with the microthermal sensor and, together with the already known thermal conductivity, the value of the thermal capacity is calculated. The sound velocity, thermal conductivity and thermal capacity are subsequently used for the correlation of the specific quantities for the gas quality, e.g. the calorific value or Wobbe index (W) or Z factor or kinematic viscosity. If necessary, the energy consumption can be determined by multiplying the mass flow with the calorific value.

Figure 5:
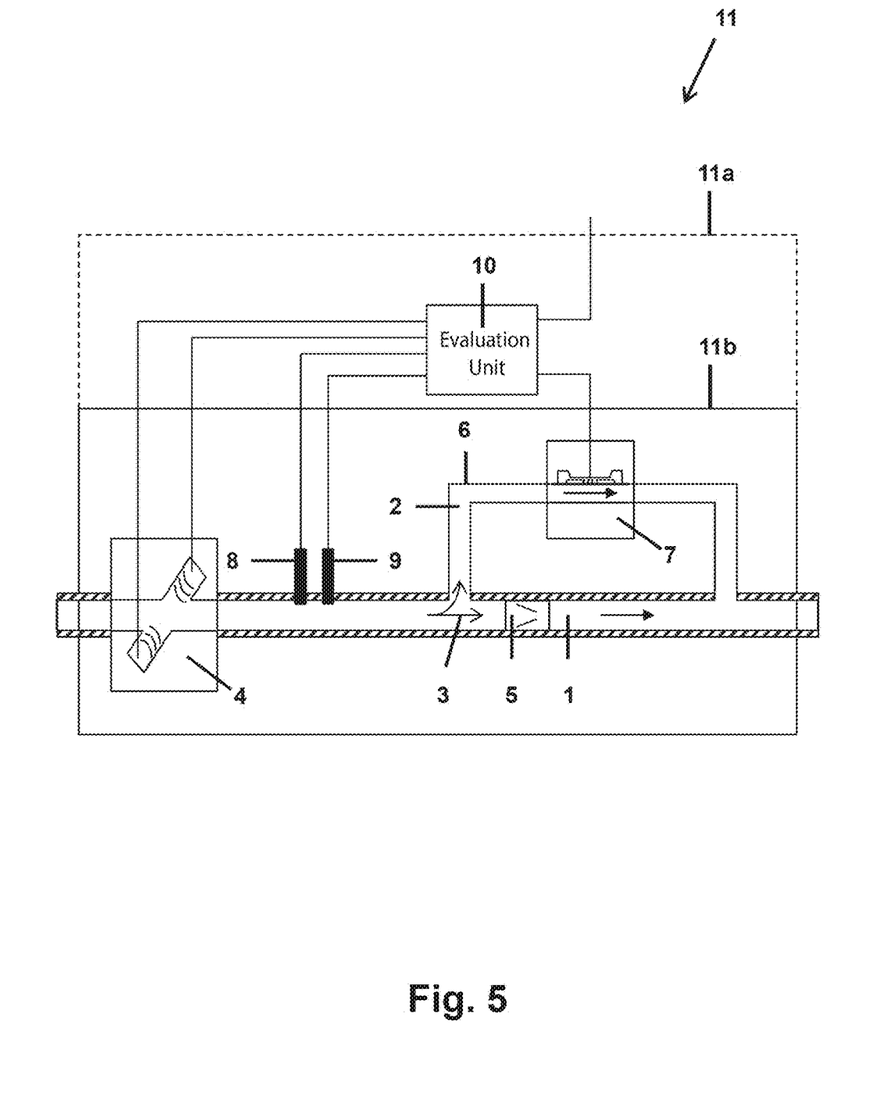
FIG. 5 shows a second embodiment of the schematic configuration of a measuring apparatus according to the present invention with a microthermal sensor in a bypass gas line to the main gas line.

FIG. 5 shows a second embodiment of the schematic configuration of a measuring apparatus 11 according to the present invention with a microthermal sensor 7 in a bypass gas line 6 to the main gas line 1. An element 5 which produces a pressure drop is provided in this case in the main gas line, so that a pressure drop is formed in operation via the bypass gas line, which leads to a gas flow 2 in the bypass gas line, wherein a characteristic flow splitting ratio 3 is obtained between the main gas line and the bypass gas line.

In the illustrated embodiment, the measuring apparatus comprises, in addition to the microthermal sensor 7, an evaluation unit 10 which is set up for carrying out a method according to the present invention, as well as an ultrasonic flow sensor 4, a pressure sensor 8 and a temperature sensor 9, which are typically arranged in the main gas line 1. Some of these components or all these components can be combined into a modular unit, wherein the evaluation unit 10 can be a component of the said modular unit (variant 11*a*), or the evaluation unit can be attached separately (variant 11*b*), e.g. in a higher-level computing unit.

The configuration in the embodiment shown in FIG. 5 is suitable both for the determination of specific quantities for the gas quality and also, in the case of the calorific value as the gas quality, for the energy consumption measurement for medium to large gas flows, which occur for example in the domestic field, in industry or in custody transfer.

The ultrasonic flow sensor 4 need not necessarily be installed in the gas line or main gas line 1, but can also be attached from the outside to the gas line or main gas line as a so-called "clamp-on device". The microthermal sensor 7 on the other hand requires only minute flow quantities and is therefore preferably arranged in a bypass gas line 6.

A second embodiment of the method for determining specific quantities for the gas quality of a gas and gas mixture according to the present invention is described below by reference to FIG. 5. In the method, the gas or gas mixture flows in a main gas line 1 over or through an element 5 producing a pressure drop. A bypass gas line 6 branches off before the element 5 producing a pressure drop and joins the main gas line again after said element. A portion of the gas or gas mixture 2 is forced by the element 5 producing the pressure drop to flow through the bypass gas line 6 and over a microthermal sensor 7 which is arranged therein. The main gas flow is supplied to the ultrasonic flow sensor 4.

The pressure and temperature of the gas or gas mixture, i.e. the operating conditions, are determined with a pressure sensor 8 and a temperature sensor 9 additionally arranged in the main gas line. The sound velocity and the flow velocity or volumetric flow are further measured with the ultrasonic sensor. This is followed by the correlation of the density on the basis of the sound velocity, wherein the density determined by means of correlation is appropriately converted to the density at the given temperature and the given pressure (operating conditions).

Furthermore, the thermal conductivity of the gas at one or several temperatures is measured with the microthermal sensor 7, in that the heating power of the heating wire is varied. If necessary, the result of this measurement can also be included in the correlation of the density. The mass flow through the main gas line 1 is subsequently calculated with the value of the density and the volumetric flow. The splitting ratio of the mass flow between the main gas line and bypass gas line is subsequently appropriately used to calculate the mass flow in the bypass gas line. The splitting ratio can be determined in advance for example in a calibration measurement with known gases.

The ratio between thermal capacity and the thermal conductivity of the gas or gas mixture is calculated from the flow factor which was also measured with the microthermal sensor and, with the already known thermal conductivity, the value of the thermal capacity is calculated. Sound velocity, thermal conductivity and thermal capacity are subsequently used for the correlation of the specific quantities for the gas quality. In the case of the calorific value as the gas quality, the multiplication of the mass flow in the main gas line with the calorific value additionally supplies the energy consumption.

Figure 6:
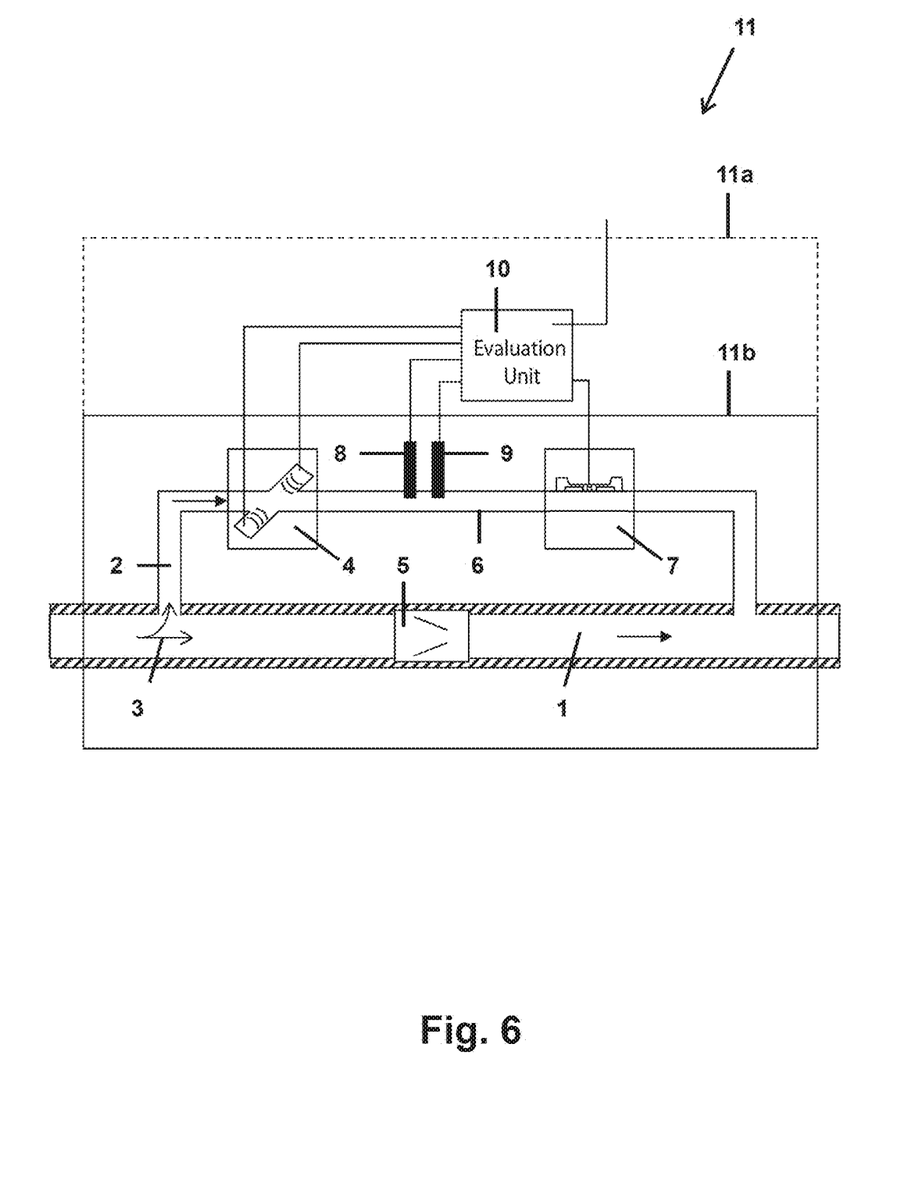
FIG. 6 shows a third embodiment of the schematic configuration of a measuring apparatus according to the present invention in a bypass gas line.

FIG. 6 shows a third embodiment of the schematic configuration of a measuring apparatus 11 according to the present invention in a bypass gas line 6 to the main gas line 1. An element 5 which produces a pressure drop is provided in this case in the main gas line, so that a pressure drop via the bypass gas line is formed in operation, leading to a gas flow 2 in the bypass gas line, wherein a characteristic flow splitting ratio 3 is formed between the main gas line and the bypass gas line.

In the illustrated embodiment, the measuring apparatus comprises an evaluation unit 10 which is set up to carry out a method according to the present invention, as well as an ultrasonic flow sensor 4 and a microthermal sensor 7 which are arranged in the bypass gas line 6. The measuring apparatus further comprises a pressure sensor 8 and a temperature sensor 9, which are mostly also arranged in the bypass gas line 1. Some of these components or all of these components can be combined into a modular unit, wherein the evaluation unit 10 can be a component of the said modular unit (variant 11*a*), or the evaluation unit can be attached separately (variant 11*b*), e.g. in a higher-level computing unit.

The configuration in the embodiment shown in FIG. 6 is preferably obtained when the ultrasonic sensor 4 is formed in microtechnology, and said sensor, as also the microthermal sensor 7, require only minute flow quantities. Both sensors are then advantageously arranged in a bypass gas line 6.

A third embodiment of the method for determining specific quantities for the gas quality of a gas and gas mixture according to the present invention will be described below by reference to FIG. 6. The method is both suitable for the continuous and also for the intermittent determination of specific quantities for the gas quality or energy consumption. Optionally required connections and valves are not shown in FIG. 6.

In the third embodiment of the method, the gas or gas mixture flows in a main gas line 1 over or through an element 5 which produces a pressure drop. A bypass gas line 6 branches before the element 5 producing a pressure drop and joins the main gas line again after said element. A portion of the gas or gas mixture 2 is forced by the element 5 producing the pressure drop to flow through the bypass gas line 6 and through an ultrasonic flow sensor 4 and over a microthermal sensor 7 which are arranged in said bypass gas line. The ultrasonic flow sensor 4 and the microthermal sensor 7 are supplied with the same gas flow.

The pressure and the temperature of the gas or gas mixture, i.e. the operating conditions, are determined by a pressure sensor 8 and a temperature sensor 9 which are additionally arranged in the bypass gas line. The sound velocity and the flow velocity or the volumetric flow are further measured with the ultrasonic sensor. Correlation of the density occurs subsequently on the basis of the sound velocity, wherein the density determined by means of correlation is appropriately converted to the density at the given temperature and the given pressure (operating conditions).

Furthermore, the thermal conductivity of the gas at one or several temperatures is measured with the microthermal sensor 7, in that the heating power of the heating wire is varied. If necessary, the result of said measurement can also be included in the correlation of the density. The mass flow through the bypass gas line 6 is subsequently calculated with the value of the density and the volumetric flow.

The ratio between the thermal capacity and the thermal conductivity of the gas and, together with the already known thermal conductivity, the value of the thermal capacity is calculated from the flow factor which is also measured with the microthermal sensor. The sound velocity, thermal conductivity and thermal capacity are subsequently used for the correlation of the specific quantities for the gas quality.

Since the aforementioned measurements and calculations relate to the bypass gas line, the splitting ratio of the mass flow between the main gas line and bypass gas line is used in order to calculate the mass flow in the main gas line. The splitting ratio can be determined in advance for example in a calibration measurement with known gases. If the calorific value was determined as the specific quantity for the gas quality, the multiplication of the mass flow in the main gas line with the calorific value additionally supplies the energy consumption.

The method and the measuring apparatus according to the present invention and the aforementioned embodiments and variants for determining specific quantities for the gas quality or the energy consumption can be used in high-pressure and low-pressure gas networks, and provide a comparatively high level of precision in the determination of the aforementioned quantities due to the correlation from the three independent variables of sound velocity, thermal conductivity and thermal capacity.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A method for determining a quantity for a gas quality comprising:
   moving a gas or gas mixture through an ultrasonic flow measuring device and over a microthermal sensor;
   determining a temperature of the gas or gas mixture using a temperature sensor;
   determining a pressure of the gas or gas mixture using a pressure sensor;
   determining a flow velocity ($v_x$) or volumetric flow and determining a sound velocity ($c_s$) of the gas or gas mixture based on information sensed by the ultrasonic flow sensor;
   determining a density of the gas or gas mixture based on a correlation with the sound velocity ($c_s$);
   calculating a mass flow of the gas or gas mixture based on the density and flow velocity ($v_x$) or the volumetric flow;
   determining a thermal conductivity of the gas or gas mixture at one or several temperatures;
   determining a flow factor ($\varphi$) based on a flow signal of the microthermal sensor;
   determining a thermal capacity ($c_p$) or a quantity dependent on the thermal capacity from the flow factor ($\varphi$) and the mass flow and the thermal conductivity; and
   determining the quantity for the gas quality using a correlation with the sound velocity and the thermal conductivity and either the thermal capacity or the quantity depending on the thermal capacity.

2. The method according to claim 1, further comprising converting the sound velocity ($c_s$) to a sound velocity at a standard temperature ($T_{norm}$).

3. The method according to claim 1, wherein the thermal conductivity and the sound velocity are used in a preciser correlation to determine the density.

4. The method according to claim 1, wherein the density is a density at a standard condition or at operating conditions.

5. The method according to claim 1, wherein the determining of the quantity of the gas quality includes using the sound velocity, the thermal conductivity information, and the thermal capacity or the quantity depending on thermal capacity in a correlation to determine at least one of a calorific value, a Wobbe index (W), a Z factor and a kinematic viscosity.

6. The method according to claim 5, further comprising calculating a value for energy consumption based on the calorific value and the volumetric flow or the mass flow.

7. A measuring apparatus for determining a quantity for a gas quality or for determining energy consumption comprising:
   an ultrasonic flow sensor configured to measure at least one of a sound velocity and a flow velocity of the gas,
   a pressure sensor configured to measure a pressure of the gas,
   a temperature sensor configured to measure a temperature of the gas,
   a microthermal sensor configured to measure at least one of a thermal conductivity of the gas and a thermal capacity of the gas or a quantity dependent on the thermal capacity, and
   an evaluation unit configured to determine the quantity for the gas quality or the energy consumption based on the sound velocity, the thermal conductivity and either the thermal capacity or the quantity dependent on the thermal capacity.

8. The measuring apparatus according to claim 7, wherein the ultrasonic flow sensor and the microthermal sensor are arranged in a gas line.

9. The measuring apparatus according to claim 8, wherein the ultrasonic flow sensor is not invasive to the gas line.

10. The measuring apparatus according to claim 7, wherein the ultrasonic flow sensor is arranged in a main gas line and the microthermal sensor is in a bypass gas line to the main gas line, and an element in the main gas line produces a pressure drop in the main gas line which generates a mass flow in the bypass gas line.

11. The measuring apparatus according to claim 10, wherein a splitting ratio between the mass flow in the bypass gas line and in the main gas line is a known value.

12. The measuring apparatus according to claim 7, wherein the ultrasonic flow sensor and the microthermal sensor are arranged in a bypass gas line to a main gas line, and an element in the main gas line produces a pressure drop in the main gas line which generates a mass flow in the bypass gas line.

13. The measuring apparatus according to claim 7, further comprising a section of a gas line in which at least one of the sensors of the measuring apparatus is arranged.

14. The measuring apparatus according to claim 7, wherein the measuring apparatus forms a modular unit including the evaluation unit, or wherein the measuring apparatus forms a modular unit without the evaluation unit, and the evaluation unit is implemented in a separate computing unit.

15. The measuring apparatus according to claim 7, wherein the evaluation unit is further configured to carry out the method comprising:

moving a gas or gas mixture through an ultrasonic flow sensor and over a microthermal sensor;

determining a temperature and pressure of the gas or gas mixture;

determining a flow velocity ($v_x$) or volumetric flow and determining a sound velocity ($c_s$) of the gas or gas mixture based on information sensed by the ultrasonic flow sensor;

determining a density of the gas or gas mixture based on a correlation with the sound velocity ($c_s$);

calculating a mass flow of the gas or gas mixture based on the density and flow velocity ($v_x$) or the volumetric flow;

determining a thermal conductivity of the gas or gas mixture at one or several temperatures;

determining a flow factor ($\varphi$) based on a flow signal of the microthermal sensor;

determining a thermal capacity ($c_p$) or a quantity dependent on the thermal capacity from the flow factor ($\varphi$) and the mass flow and the thermal conductivity; and determining the quantity for the gas quality using a correlation with the sound velocity and the thermal conductivity and either the thermal capacity or the quantity depending on the thermal capacity.

16. A method to determine a value of a gas quality comprising:

collecting information regarding a flow of a gas or gas mixture using an ultrasonic flow sensor, a microthermal sensor, temperature sensor, and a pressure sensor;

based on the collected information, calculating parameters for the flow including at least one of a flow velocity and volumetric flow, a sound velocity, a density, a thermal conductivity, and a flow factor derived from the flow signal of the microthermal sensor;

using the parameters, calculating for the flow a mass flow and a thermal capacity or a factor dependent on the thermal capacity of the flow, and determining the value of the gas quality based on the sound velocity, the thermal conductivity and the thermal capacity or the factor dependent on the thermal capacity.

17. The method of claim 16 wherein the value is at least one of a calorific value, a Wobbe index (W) value, a Z factor and a kinematic viscosity value.

* * * * *